(12) United States Patent
Dosier

(10) Patent No.: US 9,428,418 B2
(45) Date of Patent: *Aug. 30, 2016

(54) PRODUCTION AND MANUFACTURE WITH ENZYMES AND BACTERIA

(71) Applicant: BioMason, Inc., Research Triangle Park, NC (US)

(72) Inventor: Ginger K. Dosier, Raleigh, NC (US)

(73) Assignee: BioMason, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/939,118

(22) Filed: Nov. 12, 2015

(65) Prior Publication Data

US 2016/0068438 A1 Mar. 10, 2016

Related U.S. Application Data

(63) Continuation of application No. 14/270,846, filed on May 6, 2014, now Pat. No. 9,199,880, which is a continuation-in-part of application No. 13/834,273, filed on Mar. 15, 2013, now Pat. No. 8,951,786, which is a continuation-in-part of application No. 13/093,335, filed on Apr. 25, 2011, now Pat. No. 8,728,365.

(60) Provisional application No. 61/328,233, filed on Apr. 27, 2010.

(51) Int. Cl.

| | | |
|---|---|---|
| C04B 24/12 | (2006.01) | |
| C04B 28/10 | (2006.01) | |
| C04B 40/00 | (2006.01) | |
| C04B 24/14 | (2006.01) | |
| C04B 35/632 | (2006.01) | |
| C12P 1/04 | (2006.01) | |
| C04B 103/00 | (2006.01) | |

(52) U.S. Cl.
CPC .............. *C04B 24/14* (2013.01); *C04B 24/12* (2013.01); *C04B 28/10* (2013.01); *C04B 35/632* (2013.01); *C04B 40/0039* (2013.01); *C12P 1/04* (2013.01); *C04B 2103/0001* (2013.01)

(58) Field of Classification Search
None
See application file for complete search history.

(56) References Cited

U.S. PATENT DOCUMENTS

| 4,617,326 A | 10/1986 | Bjornberg et al. |
|---|---|---|
| 5,143,155 A | 9/1992 | Ferris et al. |

(Continued)

FOREIGN PATENT DOCUMENTS

| CA | 2591097 | 6/2006 |
|---|---|---|
| CN | 101270369 A2 | 9/2008 |

(Continued)

OTHER PUBLICATIONS

PCT International Search Report; PCT/US0211/033920; Jul. 22, 2011; Dosier, Ginger Krieg.
Day, Jeremy L. et al, Microbiologically Induced Sealant for Concrete Crack Remediation, http://www.ce.washingtonedu/em2003/proceedings/papers/352.pdf.

(Continued)

*Primary Examiner* — Mary F Theisen
(74) *Attorney, Agent, or Firm* — Remenick PLLC

(57) ABSTRACT

Methods for producing construction material utilizing loose pieces of aggregate (30), enzyme producing bacteria, an amount of urea and an amount of calcium ions. A first solution is prepared which includes urease which is formed by enzyme producing bacteria. A second solution is prepared which includes urea and calcium ions. The first and second solutions are added to the loose aggregate (30). The calcium ions contribute to the formation of calcium carbonate wherein the calcium carbonate fills and bonds between at least some of the gaps between the loose pieces of aggregate forming a solid construction material (92).

33 Claims, 9 Drawing Sheets

(56) References Cited

U.S. PATENT DOCUMENTS

| | | |
|---|---|---|
| 5,891,205 A | 4/1999 | Picardi et al. |
| 6,348,147 B1 | 2/2002 | Long |
| 8,182,604 B2 | 5/2012 | Kucharski et al. |
| 8,420,362 B2 | 4/2013 | Crawford et al. |
| 8,728,365 B2 | 5/2014 | Dosier |
| 8,912,244 B2 | 12/2014 | Vitomir et al. |
| 8,932,400 B2 | 1/2015 | Chen et al. |
| 8,951,786 B1 | 2/2015 | Dosier |
| 9,074,134 B2 | 7/2015 | Bang et al. |
| 9,199,880 B2 | 12/2015 | Dosier |
| 2005/0103234 A1 | 5/2005 | McNulty, Jr. |
| 2008/0245272 A1 | 10/2008 | Kucharski et al. |
| 2010/0086367 A1 | 4/2010 | Darson-Baulleur et al. |
| 2011/0027850 A1 | 2/2011 | Crawford et al. |

FOREIGN PATENT DOCUMENTS

| | | |
|---|---|---|
| EP | 0388304 | 9/1990 |
| EP | 0631998 | 1/1995 |
| EP | 1838642 | 10/2007 |
| EP | 1893546 | 3/2008 |
| EP | 2082999 A1 | 7/2009 |
| EP | 2247551 | 11/2010 |
| EP | 2297062 | 3/2011 |
| EP | 2429970 | 3/2012 |
| EP | 2462232 | 6/2012 |
| JP | 5284646 | 7/2008 |
| WO | WO2006/066326 A1 | 6/2006 |
| WO | WO2007/070706 A2 | 6/2007 |
| WO | WO 2008120979 | 10/2008 |
| WO | WO2010/130712 A1 | 11/2010 |

OTHER PUBLICATIONS

Dejong, Jason T. et al, Bio-mediated Soil Improvement; Ecological Engineering, 2009, pp. 197-210, vol. 36, Elsevier.

Dejong, Jason T. et al, Microbially Induced Cementation to Control Sand Response to Undrained Shear, Journal of Geotechnical and Geoenvironmental Engineering, Nov. 2006, pp. 1381-1392, ASCE.

Ferris, F.G. et al, Bacteriogenic Mineral Plugging, Petroleum Society of CIM and CANMET, Paper No. 11, pp. 11-11-12.

Fritzges, Michael B. et al, Biologically Induced Improvement of Loose Sand, Proceedings of the 8th U.S. National Conference on Earthquake Engineering, Apr. 18-22, 2006, Paper No. 1691, San Francisco, US.

Gollapudi, U.K. et al, A New Method for Controlling Leaching Through Permeable Channels, Chemosphere, 1995, pp. 695-705, vol. 30, No. 4, Elsevier Science Ltd., Great Britain.

Kantzas, A. et al, A Novel Method of Sand Consolidation Through Bacteriogenic Mineral Plugging, Petroleum Society of CIM, Jun. 7-10, 1992, pp. 46-1-46-15, Paper No. CIM 92-46.

De Muynck, Willem et al, Microbial Carbonate Precipitation in Construction Materials: A Review, Ecological Engineering, 2010, pp. 118-136, vol. 36, Elsevier.

Nemati, M. et al, Modification of Porous Media Permeability, Using Calcium Carbonate Produced Enzymatically in Situ, Enzyme and Microbial Technology, 2003, pp. 635-642, vol. 33, Elsevier.

Stocks-Fischer, Shannon et al, Microbiological Precipitation of CaCO3, Soil Biology and Biochemistry, 1999, pp. 1563-1571, vol. 31, Elsevier Science Ltd.

Whiffin, Victoria S. et al, Microbial Carbonate Precipitation as a Soil Improvement Technique, Geomicrobiology Journal, 2007, pp. 417-423, vol. 24, Taylor & Francis Group, LLC.

Whiffin, Victoria S., Microbial CaCO3 Precipitation for the Production of Biocement, PhD Thesis, 2004, Murdoch University, Western Australia.

PRODUCTION AND MANUFACTURE WITH ENZYMES AND BACTERIA

REFERENCE TO RELATED APPLICATIONS

This application is a continuation of U.S. application Ser. No. 14/270,846 entitled "Methods for Making Construction Materials Using Enzyme Producing Bacteria" filed May 6, 2014, issued as U.S. Pat. No. 9,199,880 on Dec. 1, 2015, which is a continuation-in-part of U.S. application Ser. No. 13/834,273 entitled "Compositions, Tools and Methods for the Manufacture of Construction Materials with Enzymes" filed Mar. 15, 2013, issued as U.S. Pat. No. 8,951,786 on Feb. 10, 2015, which is a continuation-in-part of U.S. application Ser. No. 13/093,335 entitled "Methods for Making Construction Materials Using Enzyme Producing Bacteria" filed Apr. 25, 2011, issued as U.S. Pat. No. 8,728,365 on May 20, 2014, and claims priority to U.S. Provisional Application No. 61/328,233 filed Apr. 27, 2010, the entirety of each of which is specifically incorporated by reference.

FIELD OF THE INVENTION

The invention relates to methods for producing construction material. More particularly, it relates to methods for producing construction material using enzyme producing bacteria.

DESCRIPTION OF THE BACKGROUND

The built environment is primarily constructed using a limited palette of traditional materials: clay, concrete, glass, steel, and wood. These traditional materials contain a high-embodied energy, with components of concrete and steel mined from non-renewable resources. Although wood can be grown and harvested in a renewable manner, harvesting, processing and transportation greatly contribute to carbon dioxide production and depend on large amounts of energy and fuel resources. Approximately, forty-percent of global carbon dioxide is linked to the construction industry, primarily due to material production and disposal. Biologically grown materials can be pollution free and contain a low embodied energy, if produced as part of a local ecosystem.

Commonly used throughout history, masonry construction continues to make up a large part of the built environment, utilized for both load bearing structures and veneer construction. According to Chaisson, globally, traditional clay brick manufacturing produces over 1.23 trillion units per annum with a heavy dependency on non-renewable natural resources. Clay brick manufactured in coal-powered kilns emits approximately 1.3 pounds of carbon dioxide per unit. According to Burke, in total, brick manufacturing emits over 800 million tons of man-made $CO_2$ each year, and yet represents only one material currently used in building construction.

Fired clay bricks can be manufactured between 3-20 days, depending on the equipment and processes used. This range represents modern automated factories able to process bricks without manual labor, to the clamp method of bricks stacked around a burning fire used in many developing nations.

As an alternative to load bearing fired clay masonry, Concrete Masonry Units [CMU] are widely used as they are more economical, faster to manufacture and can serve as a structural typology for global construction. Comprised of concrete, these units are made with Portland cement, large aggregate and sand filler. According to Hanley of the United States Environmental Protection Agency, global carbon dioxide ($CO_2$) emissions from cement production were approximately 829 million metric tons of $CO_2$ in 2000.

According to DeJong, Natural cement is created through chemical deposition and chemical processes associated with weathering, and can be found in various locations on the earth's crust. The formation of natural sandstones is primarily attributed to the precipitation of calcite cement.

Urease producing *Sporosarcina Pasteurii*, a nonpathogenic, common-soil bacterium has the ability to induce the production of calcite through a chemical reaction, fusing loose aggregate. A hardened material is formed in a process referred to by Stocks-Fischer as microbial induced calcite precipitation [MICP]. Applications include environmental stabilization of contaminated soils, and encapsulation of hazardous and other contaminants in natural soils and acid mine tailings. Ramachandran and Jonkers have proposed the use of microbes to remediate cracks in concrete structures and the repair of cracks in monuments. According to DeJong and Whiffin, civil engineering researchers in the United States, Australia and the Netherlands have proposed the use of MICP for soil stabilization and erosion control.

SUMMARY OF THE INVENTION

In one aspect a method is provided for producing a solid construction material which preferably is a masonry unit such as brick. A first solution is prepared which includes urease which is formed by an enzyme producing bacteria. Preferably, the enzyme producing bacterium is *Sporosarcina Pasteurii, Sporosarcina Ureae, Proteus Vulgaris, Bacillus Sphaericus, Myxococcus Xanthus, Proteus Mirabilis, Helicobacter Pylori* or a combination thereof. Most preferably, the enzyme producing bacterium is *Sporosarcina Pasteurii*. Preferably, an amount of the enzyme producing bacteria remains in the first solution after the urease is formed. A formwork is at least partially filled with loose pieces of aggregate wherein gaps are formed between at least some of the pieces. Preferably, the aggregate is sand. An amount of the first solution is added to the loose aggregate. An amount of urea and an amount of calcium ions are added to the loose aggregate. The first solution, the urea and the calcium ions may be added to the loose aggregate simultaneously or at different times or in a different order. The calcium ions contribute to the formation of calcium carbonate. The calcium carbonate fills at least some of the gaps between the loose pieces of aggregate, bonding to the aggregate and thereby forming a solid material. The solid material is removed from the formwork. Preferably, the formwork is rotated and additional amounts of the first solution, the urea and the calcium ions are added to the loose aggregate prior to removing the solid material from the formwork.

In another aspect method is provided for producing construction material. A first solution is prepared which includes urease, which is formed by an enzyme producing bacteria. A first layer of loose pieces of aggregate are applied to a substrate wherein gaps are formed between at least some of the pieces within the first layer. A first amount of the first solution is applied to the first layer. An amount of urea and an amount of calcium ions are applied to the first layer. The first solution, the urea and the calcium ions are applied to the first layer simultaneously or at different times or in a different order. A second layer of loose pieces of aggregate are applied to the first layer so that gaps are formed between at least some of the pieces of the second layer and between at least some of the pieces at the boundary between the first and second layers. A second amount of the first solution is added to the second layer. A second amount of the urea and a second amount of calcium ions are added to the second layer. The second amount of the first solution and the second amount of the urea and the second amount of calcium ions are applied to the second layer simultaneously or at different times or in a different order. The calcium ions contribute to the formation of calcium carbonate. The calcium carbonate fills at least some of the gaps between the loose pieces of aggregate, bonding to the aggregate and thereby forming a solid material.

In another aspect a method is provided for producing construction material using a computer numerical controlled (CNC) deposition machine having at least first, second and third containers. A first solution is prepared which includes urease formed by enzyme producing bacteria. A second solution is prepared which includes calcium ions. Preferably, the second solution also includes urea. The first container is at least partially filled with the first solution. The second container is at least partially filled with the second solution. The third container is at least partially filled with an amount of loose pieces of aggregate. A first layer of loose pieces of aggregate from the third container is applied to a substrate. A first amount of the first solution is applied from the first container to the first layer. A first amount of the second solution from the second container is applied to the first layer. A first amount of urea is applied to the first layer. The first amount of the first solution, the first amount of the second solution, and the first amount of urea are applied to the first layer simultaneously or at different times or in a different order. A second layer of loose pieces of aggregate from the third container is applied to the first layer. A second amount of the first solution from the first container is applied to the second layer. A second amount of the second solution from the second container is applied to the second layer. A second amount of urea is applied to the second layer. The second amount of the first solution, the second amount of the second solution, and the second amount of urea are applied to the second layer simultaneously or at different times or in a different order. The calcium ions contribute to the formation of calcium carbonate. The calcium carbonate fills and bonds between at least some of the gaps between the pieces of aggregate whereby the first and second layers are bonded together and a solid material is formed.

In yet another aspect a method is provided for producing construction material. A solution is prepared which includes urea, calcium ions and enzyme producing bacteria. The urea and the enzyme producing bacteria react to form urease. The calcium ions in the solution contribute to the formation of calcium carbonate. An amount of loose pieces of aggregate are provided whereby gaps are formed between at least some of the pieces. The calcium carbonate containing solution is added to the aggregate. The calcium carbonate fills at least some of the gaps between the loose pieces of aggregate, bonding to the aggregate and thereby forming a solid material.

As used herein, the term "bacteria" includes a single type of bacteria or a mix of multiple types of bacteria. Also as used herein, the term "formwork" includes frames, forms, molds, and other apparatus which may be used to hold loose pieces of aggregate together before the pieces are bonded in accordance with the teachings of this invention. Also as used herein, the term "solid construction material" includes construction material which is porous and non-porous.

Embodiments of the invention utilize MICP and methods are defined to fabricate full-scale construction materials, including load bearing masonry which may be pre-cast. The benefits of a construction material that can be "grown" go beyond issues of economy and sustainability. As this is a material made by aggregation, additional materials can be added to the composite for additional performance traits, such as fibers for additional strength, Titanium Dioxide [$TiO_2$] for pollution absorption, glass beads for the transmission of light, and/or air-entrained aggregates for insulation. MICP materials mimic the properties of natural sandstone and are composed of similar crystalline formations. Unique nucleic acid sequences or other identifiable tags such as unique chemical codes can be included into the compositions of the invention.

Other embodiments and advantages of the invention are set forth in part in the description, which follows, and in part, may be obvious from this description, or may be learned from the practice of the invention.

DESCRIPTION OF THE INVENTION

Figure 1:
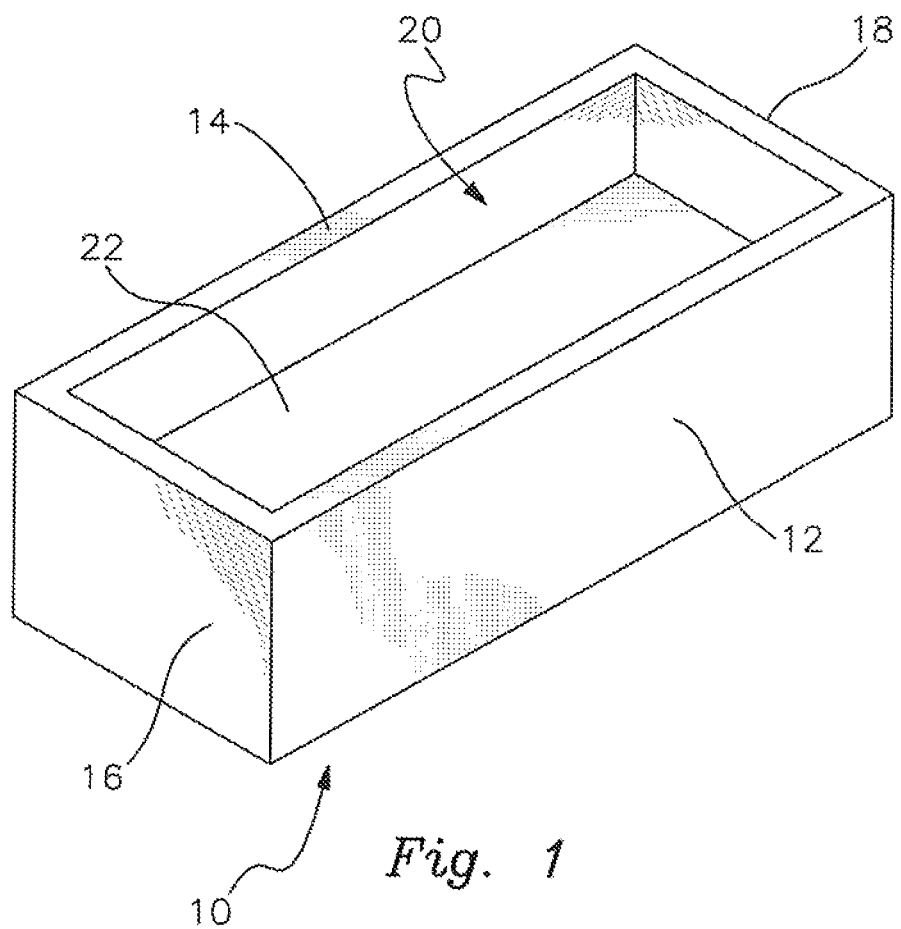
FIG. 1 is a perspective view of a formwork which may be used in connection with the manufacture of construction material embodying the invention.

*Sporosarcina Pasteurii*, a nonpathogenic common soil bacteria, has the ability to induce a cement material that can fuse loose aggregate, such as grains of sand. Other aggregates such as glass beads, recycled glass foam, fly ash composite, soil, small stones, basalt, fibers, and mixtures of the above may also be used. Ideally, local aggregate would be used from, distilled directly from the location where the units are to be manufactured. If the pieces of aggregate, such as sand, are fused in a formwork or deposited in layers and treated in accordance with the teachings of this invention, construction materials, which are preferably masonry units such as brick, may be manufactured. The teachings of this invention could further be used to produce pre-cast elements such as panels, columns, tiles, countertops, and/or any other construction unit commonly produced using clay, concrete, and/or stone. A hardened material is formed in a process known as microbial induced calcite precipitation [MICP]. The bacteria may be mixed in a solution of urea and calcium chloride. According to Ramachandran, the bacteria produce an enzyme, which in this case is urease, and use urea as a source of energy, producing ammonia and carbon dioxide, increasing the pH level of the solution. The rise in pH forms a mineral "precipitate," combining calcium chloride with carbon dioxide. The bacteria can then act as nucleation sites, attracting mineral ions from the calcium chloride to the cell wall, forming calcite crystals. The mineral growth fills gaps between the sand grains, biocementing or bonding them together. Preferably, the gaps are at least 5 microns in width. The resulting material exhibits a composition and physical properties similar to naturally formed sandstone.

It is believed that other enzyme producing bacteria that have potential for biocementation include *Sporosarcina Ureae, Proteus Vulgaris, Bacillus Sphaericus, Myxococcus Xanthus, Proteus Mirabilis* and *Helicobacter Pylori*, although proper concerns should be given to pathogenic strains.

This method for manufacturing construction materials through induced cementation exhibits low embodied energy, and can occur in a range of temperatures, e.g., below 40° C., substantially less than traditionally manufactured construction materials. Traditional brick and concrete construction is heavily reliant on burning natural resources such as coal and wood. This reliance results in increased carbon dioxide emissions and a greater dependency on limited energy sources. The introduction of a bioengineered building unit using sand aggregate and naturally induced cementation offers a natural alternative that may be locally produced and environmentally friendly.

One objective of this invention is to produce a "grown" construction material, such as a brick, utilizing primarily minerals, MICP and loose aggregate, such as sand. The teachings of this invention could further be used to produce pre-cast elements such as panels, columns, tiles, countertops and/or any other construction unit commonly produced using sand, gravel, asphalt, clay, brick, concrete, and/or stone, any of which may be recycled material.

As collaboration between architecture and microbiology, this invention enables one to use MICP, in conjunction with local sand aggregate, for the creation of a "biologically grown" building material, to be used by the construction industry. "Brick" manufacturing can be achieved utilizing traditional casting methods, or articulated by digital tooling to fabricate layered units with a programmed material composition. The use of computer numerical controlled (CNC) manufacturing technologies is economically driven as it generates little waste, accommodates a variety of potential materials, provides a high degree of accuracy, and allows for the mass customization of form, consistency, and material distribution. The brick can be digitally modeled to specifically and precisely locate mineral templates for growth, and different sizes of aggregate for intended performance. Programmed, layered growth allows for the ability to vary dimensions within the brick, just as bone varies in orientation and density throughout its length, becoming thicker and thinner in places.

These biological bricks do not require the traditional use of Portland cement mortar, rather they use the same process during biomanufacture for connection. During the construction process, the completed bricks may be "dunked" into a slurry of bacteria, growth media, and/or aggregate prior to placing them together. The bricks fuse over a period of time as the bacterially induced precipitation bonds the aggregate grains together, preferably with calcite.

This invention enables the reduction of atmospheric carbon dioxide by offering an alternative to the high-embodied energy traditionally manufactured construction materials. Employing bacteria to naturally induce mineral precipitation, combined with local aggregate and rapid manufacturing methods, this invention enables the production of a local, ecological, and economic building material for use throughout the global construction industry.

In accordance with one embodiment of this invention, a formwork, such as formwork 10 shown in FIG. 1, is used to contain the aggregate, such as sand, while the aggregate is being treated with solution or solutions containing urease, calcium ions, urea and preferably, an enzyme producing bacteria. Preferably, the urease is formed by exposing an amount of urea to the enzyme producing bacteria, such as *Sporosarcina Pasteurii*. Formwork 10 includes first, second, third and fourth vertical walls 12, 14, 16 and 18, which are connected together forming cavity 20 therebetween. Cavity 20 is adapted to receive the loose pieces of aggregate such as sand. Formwork 10 may also have a floor 22. Alternatively, the bottom of the formwork may be left open if supported by a porous surface such as soil. Preferably, vertical walls 12, 14, 16 and 18 or at least the inside surfaces thereof, are made of a non-reactive, non-porous material such as cast or extruded acrylic resin. This enables one to easily remove the construction material or the brick from the formwork 10 after it has solidified. In addition, the vertical walls and floor of formwork 10 may have textures to form textures in the resulting brick.

Figure 2:
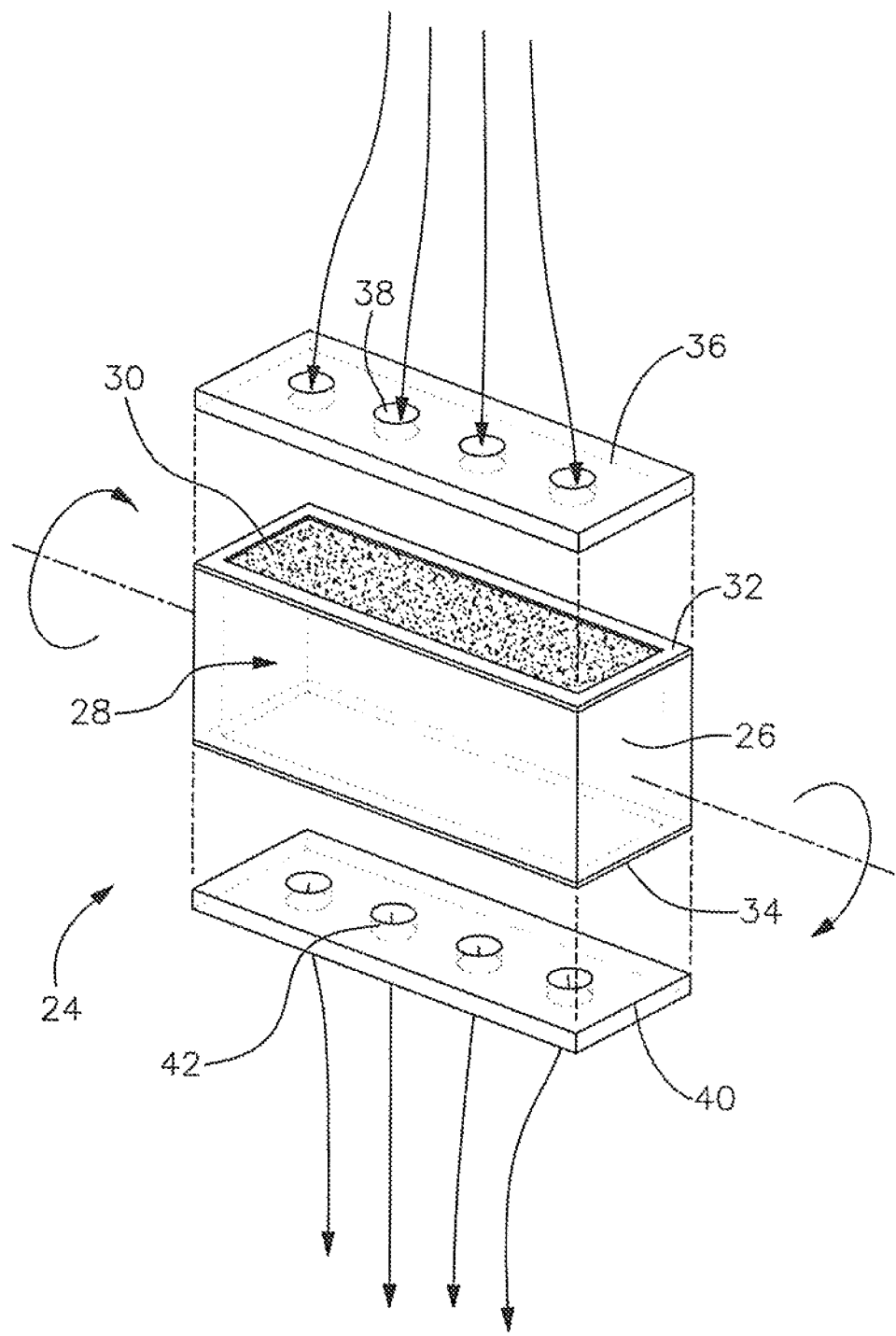
FIG. 2 is an exploded pictorial view showing another embodiment of the formwork of FIG. 1.
Figure 11:
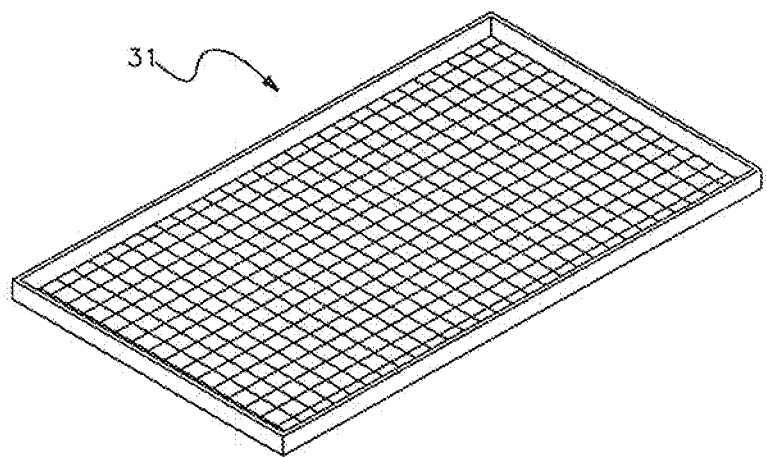
FIG. 11 is a perspective view of a screen which may be used to filter pieces of aggregate material in accordance with the teachings of this invention.

FIG. 2 shows, an alternative of the formwork of FIG. 1 which is able to be rotated so that the solutions more fully penetrate into the sand for more uniform cementation. Formwork 24 includes four vertical side walls 26 made of non-porous non-reactive material as described in reference to FIG. 1. Cavity 28, formed by the vertical side walls 26, is filled with an aggregate material 30, such as sand. Preferably, the pieces of aggregate are filtered by a known aggregate filter, such as screen 31 shown in FIG. 11, so that specific aggregates with specific consistencies and make-up may be placed in the formwork. Alternatively, thin layers of aggregate may be added to cavity 28 over time with each layer being separately treated with the solutions. The top and bottom of side walls 26 include moisture seals 32 and 34. A top removable panel 36 interfaces with moisture seal 32. The top removable panel is also made of non-porous non-reactive material. The top removable panel 36 includes a plurality of influent openings 38. A bottom removable panel 40 interfaces with moisture seal 34. The bottom removable panel is also made of non-porous non-reactive material. The bottom removable panel 40 includes a plurality of effluent openings 42. As will be described below, when formwork 24 is rotated 180°, the effluent openings 42 become influent openings and vice versa. Influent openings 38 and effluent openings 42 may be connected to hoses (not shown) to permit application and drainage of solutions containing urease, calcium ions, urea and preferably the bacteria. As cementation primarily occurs near the top portion of the aggregate material, that cementation can block the passage of additional amounts of solution further into the interior of the aggregate material. The embodiment of FIG. 2 permits the formwork 24 to be rotated, which in this embodiment is 180°, so that the openings 42 of bottom panel 40 become influent openings and the openings 38 of top panel 36 become effluent openings. This rotational feature enables better penetration of the solutions into the aggregate. The use of a plurality of influent openings provides for a more equal distribution of the solutions. In addition, the inner faces of the vertical walls 26 and the panels 36 and 42 may be textured, enabling better physical connections during assembly and/or for giving an aesthetic appeal to the bricks. In addition, a positive bump out on the inside surface of one or more of the vertical walls 26 and/or the inside surface of one or more of the panels 36 and/or 40, may be provided so that the resulting brick will have a hollowed out region or regions.

Figure 10:
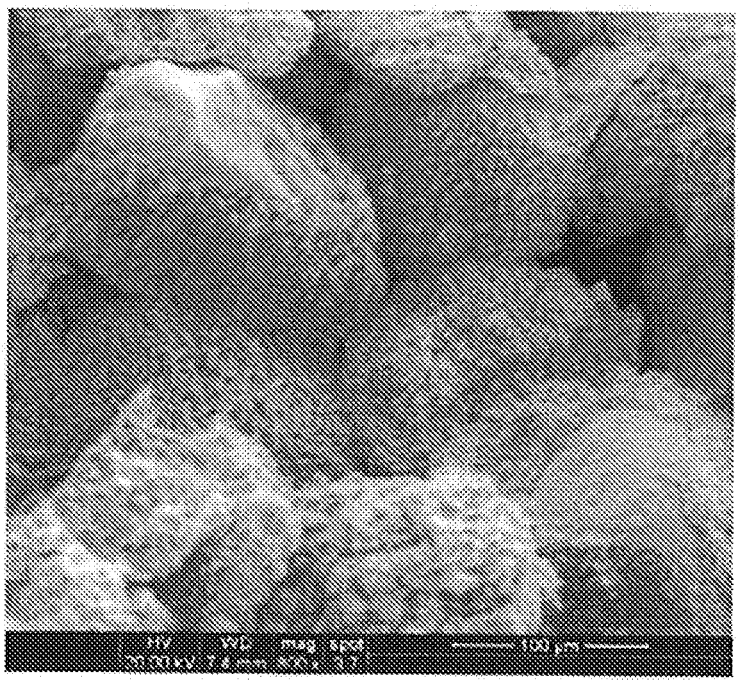
FIG. 10 is a photomicrograph showing bonding of certain gaps between loose pieces of aggregate with calcium carbonate.

The embodiment of FIG. 2 enables the solutions to be added to the aggregate purely by gravitational means without the requirement to mechanically force the solutions into the aggregate. The rotation of formwork 24 after a number of treatments ensures homogeneity in cementation and strength. Calcium carbonate crystals will grow along these aggregate surfaces where solutions are found, due to the surface tension along the pore throat formed between the aggregates. Rotation helps to ensure the equal growth of calcium carbonate around aggregate particles. The bonding of the calcium carbonate to adjacent aggregate particles is illustrated in FIG. 10. To achieve an even higher cementation depth, the formwork can be rotated along multiple axes for access to all sides. For example, if a six sided rectangular brick is desired, there are three possible axes for rotation. The embodiment of FIG. 2 shows a single axis of rotation. In addition, this rotational method can be used in conjunction with the lamination or layered method which will be described below.

Figure 3:
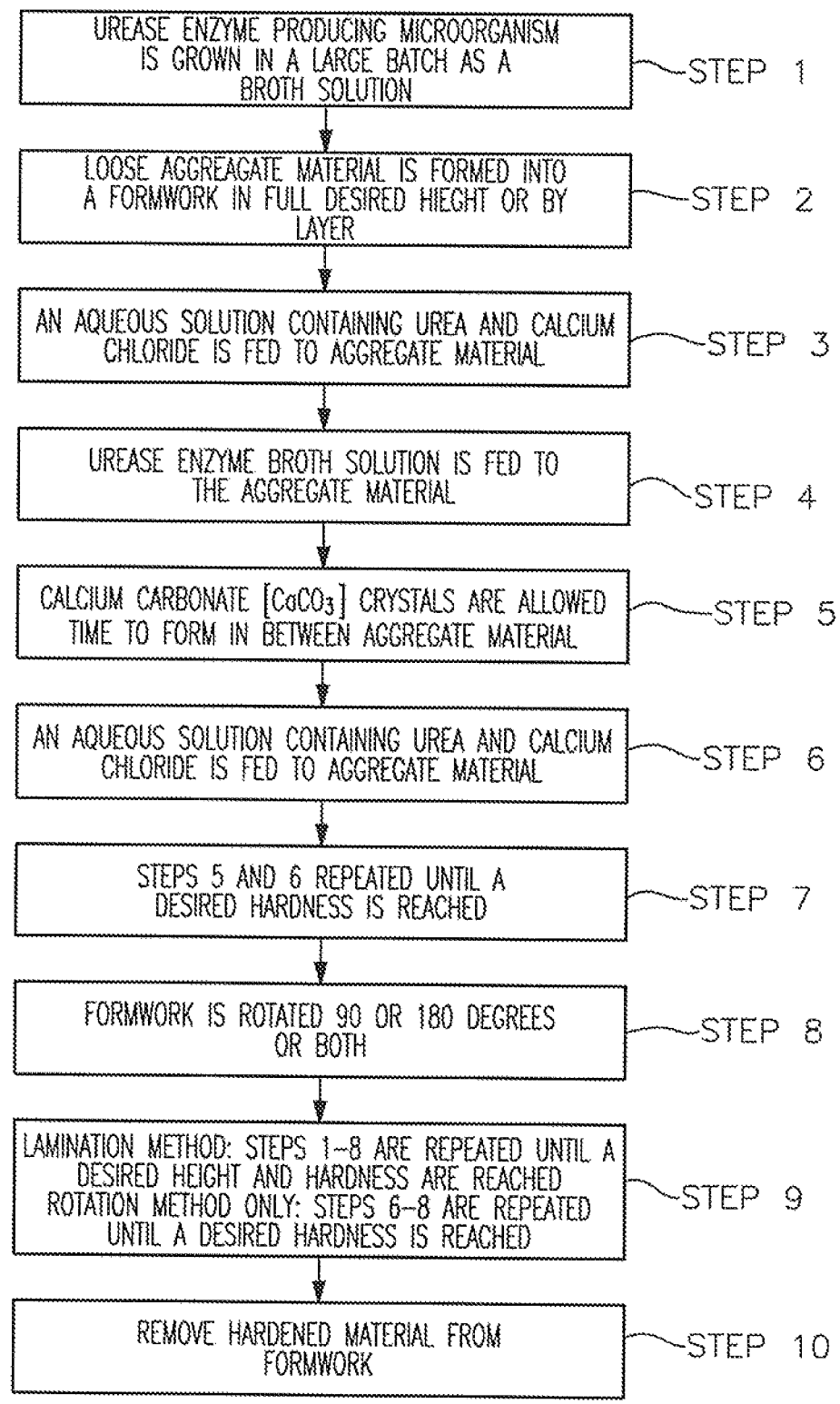
FIG. 3 is a flow chart showing steps for the production of construction material in accordance with one embodiment of the invention.

Steps 1 through 8 of FIG. 3 illustrate the rotational method of manufacturing the brick. Step 9 of FIG. 3, when combined with Steps 1 through 8, illustrates the combination of the rotational method and lamination method. In the lamination method, discrete layers of aggregate are separately deposited and individually treated with the solutions.

Referring now more particularly to FIG. 3, in Step 1, a urease producing bacteria is grown as a broth solution. The preferred urease producing bacteria are *Sporosarcina Pasteurii, Sporosarcina Ureae, Proteus Vulgaris, Bacillus Sphaericus, Myxococcus Xanthus, Proteus Mirabilis*, and *Helicobacter Pylori*. The most preferred urease producing bacteria is *Sporosarcina Pasteurii* in part due to it being non-pathogenic. In addition, growth material such as yeast extract or peptone from soy is added to the broth to help enable the bacteria to multiply. In Step 2, loose pieces of aggregate material, such as sand, is inserted into the cavity 30 of formwork 24 to the desired height. In the lamination method, only a relatively thin layer of loose aggregate is added. Gaps are formed between at least some of the pieces of aggregate material. In Step 3, an aqueous solution containing urea and a source of calcium ions, such as calcium chloride, is fed to the aggregate material. In Step 4, the urease enzyme broth solution, preferably containing the bacteria, is fed to the aggregate material. Steps 3 and 4 may be done simultaneously or at different times or in different order. In addition, the urea and the calcium ions may be in the same or different solutions. In Step 5, calcium carbonate crystals form between at least some of the gaps between the loose pieces of aggregate material. In Step 6, it is preferred that additional aqueous solution containing urea and calcium ions is fed to the aggregate material to reach the desired hardness of the brick. In Step 7, Steps 5 and 6 may be repeated until a desired hardness is reached. In Step 8, the formwork 24 is rotated, which in the embodiment of FIG. 2 is 180°. After rotation, Steps 1 through 7 are repeated. For combining the lamination method with the rotational method, in Step 2, the formwork 24 is not completely filled with aggregate but is only partially filled so as to form a layer. The solutions are applied to that layer of aggregate as set forth in Steps 3 through 7 and then the formwork may be rotated as set forth in Step 8. Once that layer has reached a degree of hardness, an additional layer of aggregate is fed to formwork 24 over the top of the hardened layer and Steps 3 through 8 are repeated. Additional layers can also be formed in a like manner.

Figure 4:
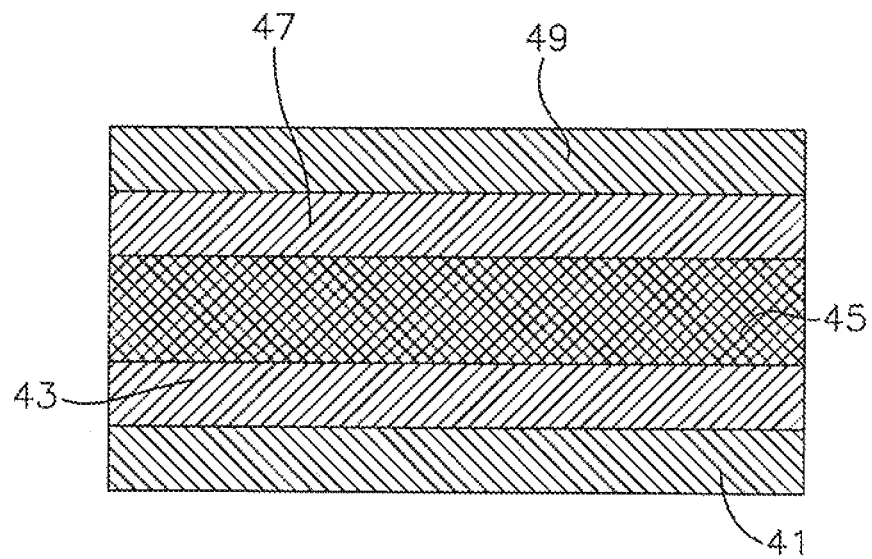
FIG. 4 is a side elevational view showing multiple layers of bonded aggregate formed using the embodiment of FIGS. 2 and 3.

FIG. 4 illustrates the striations or layers formed by the combination of the lamination and rotational methods referred to above. Layers 41, 43, 45, 47 and 49 are discrete layers. The sand within each layer is bonded and the sand at the boundaries of adjacent layers is also bonded forming a solid brick. The layering or lamination method allows for a programmed structure for the brick, for example, larger aggregate and particle distribution. It also allows for homogeneity of cementation. The calcium carbonate crystals, which form the bonds, are allowed to grow in between the layers so as to bond the layers together. The layering method of fabricating biomanufactured construction material allows for greater consistency in cementation and possibly over-all structural performance. The layering of the aggregate material allows for programmed structure and distribution of aggregate particle sizes, that is, larger aggregate particles may be used as structure.

Figure 6:
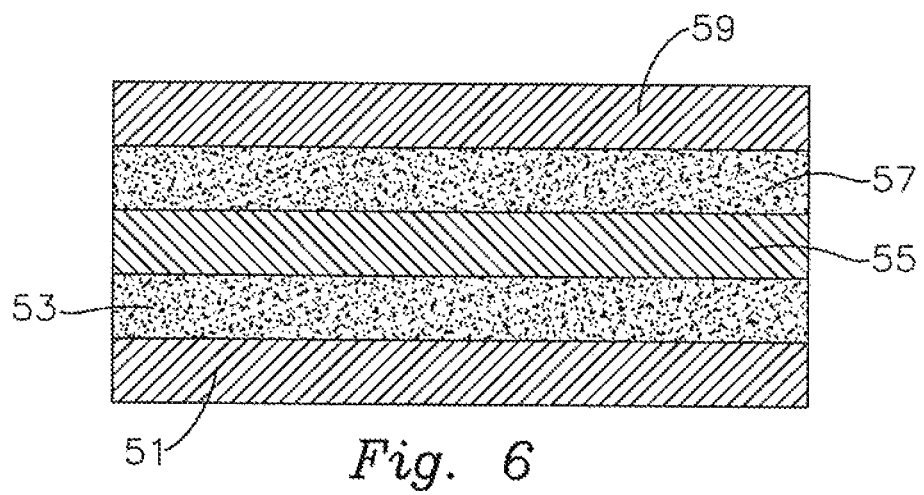
FIG. 6 is a side elevational view also showing multiple layers of bonded aggregate formed using the embodiment of FIGS. 5 and 6.

The preferred embodiment of carrying out the layering or lamination method is through the use of a computer numerical controlled (CNC) deposition machine, such as a 3-D printer, an embodiment of which is illustrated in FIG. 6, although other means may be employed, including manually layering by hand or mechanically layering through mass production.

Figure 5:
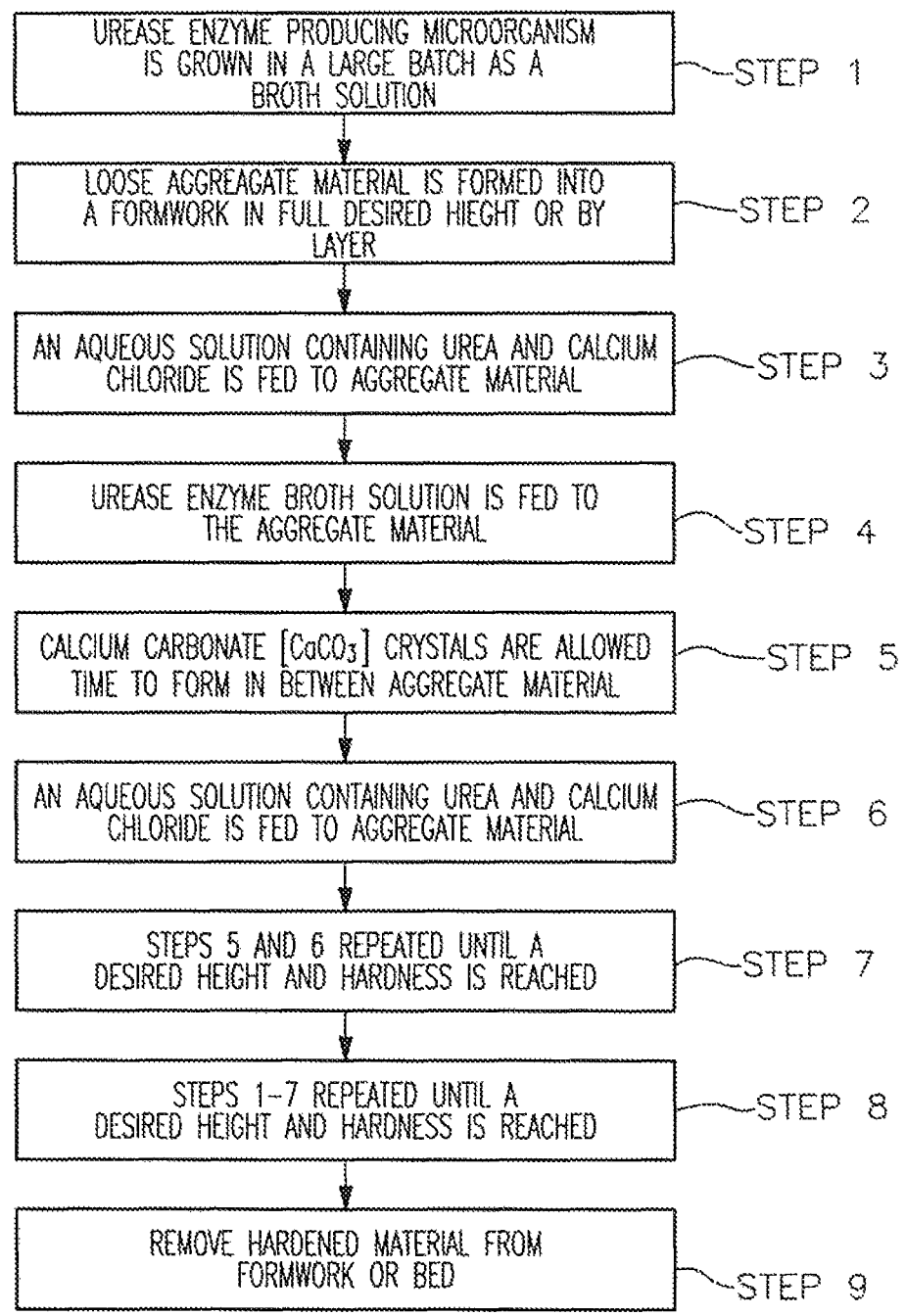
FIG. 5 is a flow chart showing steps for the production of construction material in accordance with another embodiment of the invention.

FIG. 5 illustrates an embodiment of the lamination or layering method of producing construction material. As illustrated in Step 1, urease producing bacteria, such as one of those listed above, is grown in a batch of broth solution with a growth media, such as urea, forming urease. A growth nutrient such as yeast extract or soy peptone is also added to the broth. As shown in Step 2, a layer of loose aggregate material is placed in a formwork or spread over a bed or substrate. As shown in Step 3, an aqueous solution containing urea and calcium ions, which may be obtained from calcium chloride, is fed to the aggregate material. The urease solution is fed to the aggregate material. Again, the solutions from Step 3 and Step 4 may be added to the aggregate simultaneously, at different times, or in a different order. In addition, the urea and the calcium ions may be in the same or different solutions. As shown in Step 5, calcium carbonate crystals form between the gaps in the pieces of aggregate material. As shown in Step 6, another aqueous solution containing urea and calcium chloride is fed to the aggregate material. As shown in Step 7, Steps 5 and 6 are repeated until a desired hardness is reached. As shown in Step 8, Steps 1 through 7 are repeated, thereby forming a number of layers, until a desired height and hardness are reached. As shown in Step 9, the hardened material, with the layers bonded together, is removed from the formwork, the bed or the substrate. Thus, solid layered material is formed from the loose aggregate.

FIG. 6 illustrates multiple layers which are bonded together to form the construction material which is made by the embodiment of FIG. 5. The aggregate within layers 51, 53, 55, 57 and 59 are bonded together and the adjacent layers at their boundaries are bonded together forming a solid brick.

Figure 7:
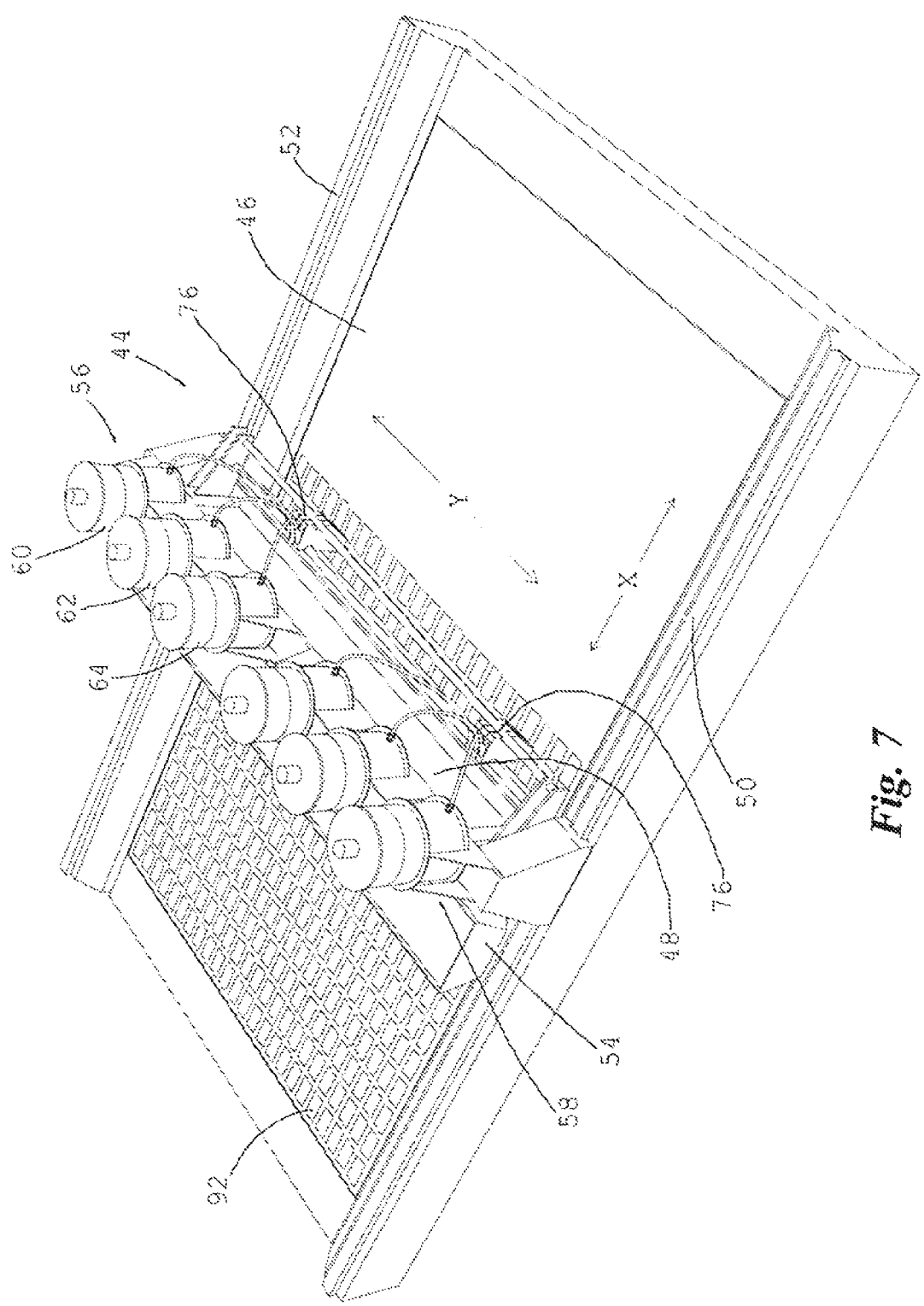
FIG. 7 is perspective view of a computer numerical controlled deposition machine which may be used to produce construction material in accordance with the teachings of an embodiment of the invention.

FIG. 7 shows a computer numerical controlled (CNC) deposition machine which may be utilized to produce construction material using the layering or lamination method. Existing computer numerical controlled (CNC) platforms may be used and are commercially available from the MultiCam company (Series 5000 Model 508), although such platforms need to be modified as discussed below. Essentially, CNC deposition machine 44 is a MultiCam Series 5000 Model 508 which has been modified by adding the items shown in FIGS. 8 and 9, and spreader 54 and bed or substrate 46 thereto. The use of CNC technology is economically driven as it generates little waste, accommodates a variety of potential materials, provides a high degree of accuracy, and allows for large variations. Thus, the individual units of construction material are not bound by repeatable formwork or conventional forms. Rather, each unit of construction material can either be the same or different depending on the desired form and utilization. CNC deposition machine 44 is a three axes computer controlled printer for producing laminated or layered construction materials utilizing the lamination or layering method of the invention. A horizontal platform or substrate 46 is provided. The platform 46 may be specified in any dimension in the X and Y axes. The platform is supported by a hydraulic lift or other elevating mechanism for producing movement vertically, i.e., in the Z axis. Gantry 48 commands the Y axis and moves along rails 50 and 52 in the X axis by utilizing stepper motors. A dispensing nozzle unit 76 moves along rails in the Y axis by utilizing stepper motors. A microprocessor coordinates X-axis, Y-axis, and Z-axis movements to accurately locate the printer nozzle in 3-Dimensional space from user provided data, such as a digital model. Elongated container 54 holds the loose pieces of aggregate, such as sand, and serves as the aggregate spreader. Container 54 extends across substantially the width of substrate 46.

CNC deposition machine 44 includes solution containment clusters, namely, cluster 56 and another cluster 58. The solution containment clusters each include three containers, namely, container 60 which contains calcium chloride whereby calcium ions are in solution, container 62 which contains urea in solution, and container 64 which contains urease enzyme solution which was formed from combining the enzyme producing bacteria, which preferably is *Sporosarcina Pasteurii*. Normally, container 64 also includes an amount of the bacteria.

Figure 8:
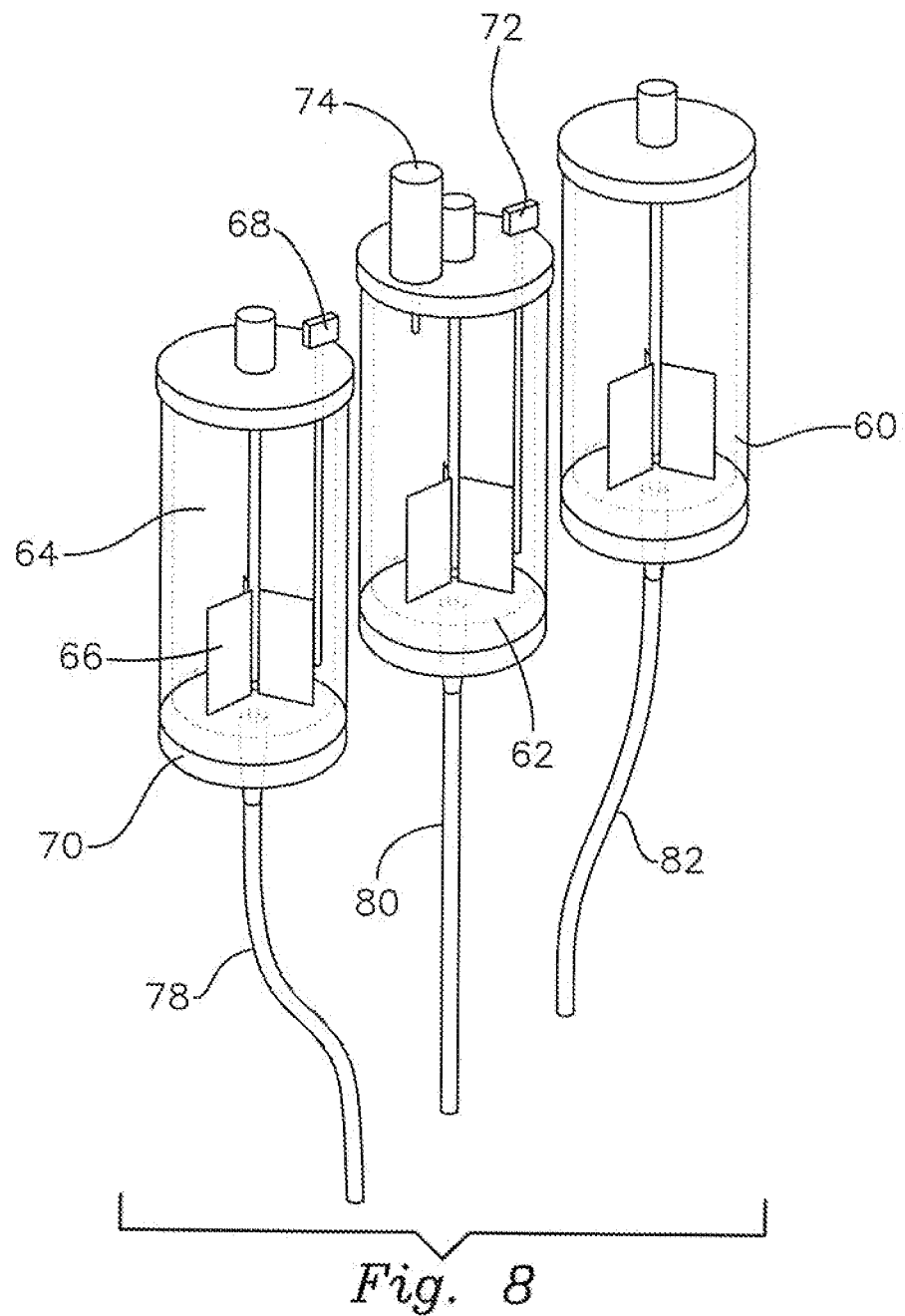
FIG. 8 is a pictorial view showing details of a portion of the computer numerical controlled deposition machine shown in FIG. 7.

FIG. 8 shows container cluster 56 in more detail. Each container 60, 62 and 64 includes a motor driven mixer 66. The motor driven mixer keeps the contained solution homogeneous. Urease enzyme solution container 64 also includes a temperature sensor 68 and warming element 70 to maintain optimum microorganism growth conditions. The urea solution container 62 includes a pH sensor 72 and a buffer solution dispenser 74 for maintaining an optimal concentration of hydrogen ions.

Figure 9:
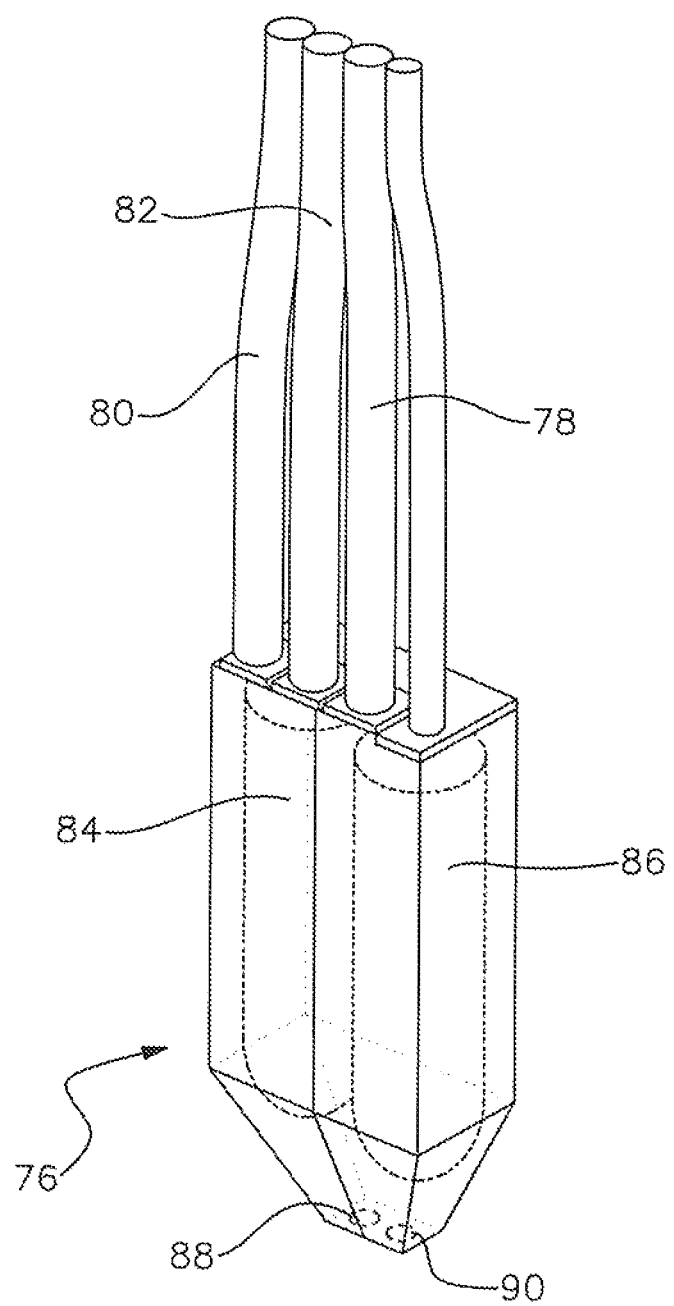
FIG. 9 is a perspective view showing details of an additional portion of the computer numerical controlled deposition machine shown in FIG. 7.

FIG. 9 illustrates a dispensing nozzle 76 for each solution containment cluster, such as cluster 56. Hoses 78, 80 and 82 connect respective containers 60, 62 and 64 to nozzle 76. Urea from container 62 is mixed with calcium ions from calcium chloride from container 60 in reservoir 84 which is received within dispensing nozzle 76. Urease enzyme and preferably an amount of bacteria are received from container 64 to reservoir 86. Opening 88 and dispensing nozzle 76 are connected to urea and calcium ions from calcium chloride reservoir 84 for applying urea and calcium ions to the layer of aggregate which has been deposited on substrate 46. Opening 90 connects to urease enzyme reservoir 86 for depositing urease enzyme solution onto the aggregate material which has been deposited on substrate 46. Computer control valves, such as solenoids, regulate the mixing of urea and calcium ions as the solutions are released from their respective reservoirs. Computer control valves also regulate the release of the solutions from the reservoirs through their respective openings 88 and 90.

The CNC deposition machine 44 operates as follows. Gantry 48 moves horizontally in one direction across the entire substrate 46 along the X axis depositing a single layer of aggregate material from aggregate container 54. Gantry 48 then returns to its initial position. Gantry 48 then moves one position along the X axis. The dispensing nozzles 76 move horizontally in another direction along the Y axis depositing an urease enzyme solution and a solution of urea and calcium ions onto individual units of sand 92, which in this embodiment are rectangular, which is specified by the user's input. The dispensing nozzles then return to their initial position. The steps of depositing the solution are repeated until gantry 48 reaches the end of the X axis whereby one layer of the construction material, such as brick, is formed. Gantry 48 then returns to its initial position. As an option, the solutions may again be deposited on the same layer of sand to achieve stronger cementation. The elevated substrate 46 then moves downwardly one position in the Z axis. The steps above are repeated until the desired material height is reached. Multiple cemented layers bonded together forming individual units are thus formed. The uncemented aggregate material, that is the aggregate material which is between individual units 92, is removed from the substrate. The layered cemented units are then removed from the substrate.

Alternatively, the solution dispenser nozzles and/or containment clusters may be utilized in conjunction with other computer numerical controlled platforms, such as six and seven axes robotic arms, for the precision location of solutions.

The following examples illustrate embodiments of the invention, but should not be viewed as limiting the scope of the invention.

EXAMPLES

Example 1

Cementation Tests

Materials

General cementation tests were performed in 60 ml cylinders with aggregate to test various method sequences and aggregate types. Consecutively, multiple formwork tests were performed in the scale of a 1:1 construction unit measuring 3.5 inches×2.25 inches×8 inches [88.90 mm×57.15 mm×203.20 mm] and a scaled version of a construction unit measuring 3 cm×1.5 cm×5 cm.

*Sporosarcina Pasteurii* [DSMZ 33] was inoculated in a "bacteria solution" DSMZ 220 media modified with urea, transferred to plate for colony growth and incubated at 25° C. for later use. General "cementation solutions" were prepared using 0.28% Tryptic Soy Broth made by Scharlau 117-333 mM urea [$(NH_2)_2CO$], 130-187 mM ammonium chloride [$NH_4Cl$], 25 mM sodium hydrogen carbonate [$NaHCO_3$], 55 mM calcium chloride [$CaCl_2$], and 1 L of distilled water. Medias were filter sterilized to insure against contamination. A concentration of 55 mM calcium chloride dihydrate was prepared as an aqueous solution for the calcium ions used in the cementation process.

Apparatus Set Up

Three 60 ml syringes were each filled with [A] 5 g Poraver™ 2 mm-1 mm [porous glass beads], [B] 30 g sieved 600–212 microns of locally sourced sand found in Sharjah, United Arab Emirates [UAE] and [C] 30 g 600–75 microns of the same sand. The samples were then vibrated for granular settlement and plungers were applied to confine the sand in the form. This process also reduces the air between grains of sand, air entrained in the system could cause a fracture point in the final hardened material due to the resulting formation of a bubble void.

A flexible 4 mm ID silicon hose was inserted into the top of the syringe plunger as an influent line, and another 4 mmID tube was inserted into the syringe bottom as an effluent line.

The tests were first fed Solution 1 "Bacteria Solution" at a gravity flow rate as approximately three pore volumes [PV] of media. After allowing the bacteria to "set" for six hours, the tests were then fed Solution 2 "Cementation Solution" as three PV of media at a gravity flow rate after which the solution was allowed to "set" for 4-12 hrs. This sequence was alternated for the UAE sand samples. This process continued until hardness was reached. The tests were flushed with tap water and allowed to air dry.

All three samples exhibited cementation. The samples were weighed to determine gained mineral material. After weighing, the samples were prepared for Scanning Electron Microscopy [SEM] to visually verify crystal formations and bonded grains of aggregate. FIG. 10 illustrates sample C.

| Sample | Starting Weight | Final Weight | Gained Weight |
| --- | --- | --- | --- |
| A Poraver ™ | 5 g | 10.21 g | 5.21 g |
| B Sharjah 600-212 microns | 30 g | 39.94 g | 9.94 g |
| C Sharjah 600-75 microns | 30 g | 37.07 g | 7.07 g |

Equipment

Bacterial colonies on plates were stored in a 25° C. incubator. The bacteria solution batches were grown aerobically with an incubated shaker set at 37° C., 250-300 RPM for 20-24 hours. A Tinius Olsen H50TK compression-testing machine was used to determine the compressive strength value of the final hardened material. As an example, the sand sample [C] reached 16.58 MPa as a compressive strength. The overall hardness and strength can be increased with additional cementation solution treatments.

Example 2

Rotation Method

To create a greater strength and more unified cementation throughout the aggregate, a rotation method was developed for a full-scale "brick" form. A batch of bacteria solution was prepared using the same method as example 1. Simultaneously, a batch of cementation solution set to 7.25 pH was prepared using the same media as example 1. 1700 g of non-sterile aggregate in the form of indigenous sand found in Sharjah, UAE was sieved to 2 mm-212 microns and placed into the formwork, after a polyester fiber filter was applied. The formwork was then vibrated to reduce air between the aggregate, another polyester fiber filter was placed on top of the dry aggregate, and the formwork top with influent holes was lastly positioned. The formwork is the same as in FIG. 2. Full scale construction unit formwork in the form of a building unit [3.5 inches×2.25 inches×8 inches] was fabricated of 5 mm cast acrylic using Universal Systems 50 Watt laser cutter for precise and reusable breakaway formwork.

15 ml of 55 mM $CaCl_2$ was added to 750 ml of the prepared cementation solution. The solution was then fed to the formwork via gravity feed through the influent holes. As soon as the effluent began to leave the formwork, the effluent valves were then shut off to "trap" the solution in the formwork between voids in the aggregate. The solution was allowed to set in the formwork for approximately 15 minutes.

750 ml of bacteria solution with live cells was then fed to the formwork via gravity feed through the influent holes. Effluent was allowed to leave the formwork until the cementation solution reached the end of the influent holes after which the effluent valves were then shut off to "trap" the solution in the formwork between voids in the aggregate. The solution was allowed to set in the formwork for 4-12 hours.

Another batch of cementation solution with urea and calcium chloride was prepared and fed to the formwork via gravity feed through the influent holes. As the effluent began to leave the formwork, the effluent valves were then shut off to "trap" the solution in the formwork between voids in the aggregate for 4-12 hours. This process was repeated again 5-10 times.

The formwork was then rotated 180 degrees along one axis with the bottom of the formwork becoming the top and the top becoming the bottom.

Another batch of cementation solution with urea and calcium chloride was prepared and fed to the formwork via gravity feed through the influent holes. As soon as the effluent began to leave the formwork, the effluent valves were then shut off to "trap" the solution in the formwork between voids in the aggregate for 4-12 hours. This process was again repeated 5-10 times.

The formwork was then rotated again 180 degrees along one axis with the bottom of the mold now being on top. Rotation and administration of cementation solution continued until a desired hardness or strength was reached. The hardened construction material was removed from the formwork, washed with tap water and allowed to air dry. After the material was dried and weighed, the resulting material was homogeneously cemented on all sides. The cemented material was mechanically split along the center and cementation was verified along the cross section of the interior.

Example 3

Slurry Method

The slurry method used the same medias and methods as the above example, with the exception that the two solutions and aggregate were combined forming an aqueous slurry of aggregate, bacteria solution, urea, and calcium chloride. The slurry was then placed in the same design of formwork as described in example 2 with the exception of a change in dimension to 3 cm×1.5 cm×5 cm. Effluent valves were shut off to "trap" the solution in the formwork between voids in the aggregate and allowed to set for 3-8 hours.

Another batch of cementation solution with urea and calcium chloride was prepared and fed to the formwork via gravity feed through the influent holes. As soon as the effluent began to leave the formwork, the effluent valves were then shut off to "trap" the solution in the formwork between voids in the aggregate for 4-12 hours. This process was repeated 5-10 times.

The formwork was then rotated along one axis with the bottom of the formwork now being on top [Side A]. Another batch of cementation solution with urea and calcium chloride was prepared and fed to the formwork via gravity feed through the influent holes. As soon as the effluent began to leave the formwork, the effluent valves were then shut off to "trap" the solution in the formwork between voids in the aggregate for 4-12 hours. This was repeated 5-10 times.

The formwork was then rotated 180 degrees along one axis with the bottom of the formwork becoming the top and the top becoming the bottom. Rotation and administration of cementation solution continued until a desired hardness and strength was reached.

The hardened material in the form of a "brick" was removed from the formwork, washed with tap water and allowed to air dry. All sides were cemented.

Example 4

Lamination Method [Analog]

The lamination method used the same medias and methods as example 2 with the exception that the aggregate material was placed into the formwork as distinct layers. This enables the final material to have different degrees of aggregate particle size distribution, and a more homogeneous cementation within the overall unit.

A 5 mm layer of non-sterile aggregate in the form of indigenous sand found in Sharjah, UAE was sieved to 600 microns–212 microns and placed into the formwork. The formwork was lightly vibrated to reduce air between aggregates.

2 ml of 55 mM $CaCl_2$ was added to 50 ml of the prepared cementation solution. The solution was then fed to the formwork via gravity feed through the influent holes. The solution was allowed to set in the formwork for approximately 15 minutes.

50 ml of bacteria solution with live cells was then fed to the formwork via gravity feed through the influent holes. The solution was allowed to set in the formwork for 4-12 hours. Another batch of cementation solution with urea and calcium chloride was prepared and fed to the formwork via gravity feed through the influent holes. This was repeated 5-10 times.

Another layer of 5 mm non-sterile aggregate was placed into the formwork, on top of Layer 1. The process as described for layer 1 was repeated until the full height and desired hardness and strength of the final unit was reached, with a total of 3 layers.

The hardened material was removed from the bed, washed with tap water and allowed to dry.

Example 5

Lamination+Rotation Method [3 cm×1.5 cm×5 cm]

The lamination+rotation method used the same medias and methods as described examples 2 and 4, with the exception of each layer being rotated and treated on both sides prior to the addition of each successive layer.

Example 6

Lamination Method [Digital Rapidly Manufactured]

A modified "Fab at Home" CNC 3D printer [open source 3D printer platform] was used to precisely deposit the solutions over a bed of sand material for rapid manufactured tests.

A batch of Solution 1 "Bacteria Solution" was prepared using the same method as example 1. Simultaneously, a batch of Solution 2 "Cementation Solution" set to 7.25 pH was prepared using the same media as example 1.

A 5 mm layer of non-sterile aggregate in the form of indigenous sand found in Sharjah, UAE was sieved to 600 microns–212 microns and placed onto the substrate bed of the 3D Printer.

1 ml of 55 mM of $CaCl_2$ was added to 25 ml cementation solution and mixed with 25 ml of the bacteria solution. This was then placed in the deposition syringe of the 3D printer.

The syringe motor was controlled via a computer model and the 51 ml of cells and cementation solution was precisely deposited as discrete droplets on top of the sand substrate as multiple passes. The deposition syringe was reloaded and cleaned as necessary.

The solutions were allowed to set in the sand for 3 hours, after which a new preparation of cementation solution was prepared and set to 7.25 pH. This new solution was placed into the syringe and deposited over the sand substrate. The solution was allowed to set in the sand for 3 hours, after which a new preparation of cementation solution was prepared and set to 7.25 pH. This process continued for a total of 5 treatments.

A new 5 mm layer of non-sterile aggregate [same composition as layer 1] was sieved to 600–425 microns and evenly placed onto the substrate over layer 1. The process as described for layer 1 was then repeated for layer 2 and again for layer 3.

A new preparation of cementation solution was prepared and set to 7.25 pH. This solution was placed in the syringe of the 3D printer and deposited over the top of the hardened sand over multiple passes. This step served as a "finishing" pass of cementation media.

The hardened material was removed from the bed, washed with tap water and allowed to dry.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

INDUSTRIAL APPLICABILITY

The way in which the invention is capable of being exploited and the way in which it can be made and used will be apparent from the foregoing.

Other embodiments and uses of the invention will be apparent to those skilled in the art from consideration of the specification and practice of the invention disclosed herein. All references cited herein, including all publications, U.S. and foreign patents and patent applications and specifically U.S. Pat. Nos. 9,199,880; 8,951,786; and 8,728,365, and U.S. Provisional Application No. 61/328,233, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method for producing construction material comprising:
   providing an amount of urease;
   providing an amount of calcium; and
   providing an amount of urea;
      wherein the amount of urease, the amount of calcium and the amount of urea when incubated with an aggregate in a formworks forms the construction material.

2. The method of claim 1, wherein the amount of urease is provided by microorganisms.

3. The method of claim 2, wherein the microorganisms comprise *Sporosarcina pasteurii, Sporosarcina ureae, Proteus vulgaris, Bacillus sphaericus, Myxococcus xanthus, Proteus mirabilis, Helicobacter pylori* or combinations thereof.

4. The method of claim 1, wherein the amount of calcium comprises calcium chloride.

5. The method of claim 1, wherein the amount of urease is combined with the amount of calcium and/or the amount of urea in an aqueous composition.

6. The method of claim 1, wherein the amount of urease, the amount of calcium, and the amount of urea provided are sufficient to form calcite.

7. The method of claim 1, wherein the incubation comprises contacting the aqueous composition with the aggregate for a period of time.

8. The method of claim 7, wherein the period of time is from 4 to 12 hours.

9. The method of claim 1, wherein the aggregate comprises one or more of sand, gravel, asphalt, clay, brick, glass, fibers, titanium, concrete, stone and/or recycled material.

10. The method of claim 1, wherein the aggregate further comprises performance enhancing materials and/or identifiable tags.

11. The method of claim 10, wherein the performance enhancing materials comprise materials for insulation, pollution control, light transmission or combinations thereof.

12. The method of claim 1, wherein the formworks comprises frames, forms, molds, or other apparatus that hold aggregate.

13. The method of claim 1, wherein the construction material comprises porous or non-porous bricks, load-bearing structures, masonry units, tile, veneer, shaped structures and combinations thereof.

14. The method of claim 1, further comprising providing a growth nutrient.

15. A method for producing construction material comprising:
   providing amounts of urease, calcium and urea in an aqueous composition;
   incubating the composition with an aggregate in a formworks; and
   forming the construction material.

16. The method of claim 15, wherein the amount of urease is provided by microorganisms.

17. The method of claim 16, wherein the microorganisms comprise *Sporosarcina pasteurii, Sporosarcina ureae, Proteus vulgaris, Bacillus sphaericus, Myxococcus xanthus, Proteus mirabilis, Helicobacter pylori* or combinations thereof.

18. The method of claim 15, wherein the amount of calcium comprises calcium chloride.

19. The method of claim 15, wherein the amount of urease is combined with the amount of calcium and/or the amount of urea in an aqueous composition.

20. The method of claim 15, wherein the amount of urease, the amount of calcium, and the amount of urea provided are sufficient to form calcite.

21. The method of claim 15, wherein the incubation comprises contacting the aqueous composition with the aggregate for a period of time.

22. The method of claim 21, wherein the period of time is from 4 to 12 hours.

23. The method of claim 15, wherein the aggregate comprises one or more of sand, gravel, asphalt, clay, brick, glass, fibers, titanium, concrete, stone and/or recycled material.

24. The method of claim 15, wherein the aggregate further comprises performance enhancing materials and/or identifiable tags.

25. The method of claim 24, wherein the performance enhancing materials comprise materials for insulation, pollution control, light transmission or combinations thereof.

26. The method of claim 15, wherein the formworks comprises frames, forms, molds, or other apparatus that hold aggregate.

27. The method of claim 15, wherein the construction material comprises porous or non-porous bricks, load-bearing structures, masonry units, tile, veneer, shaped structures and combinations thereof.

28. The method of claim 15, further comprising rotating the formwork and adding an additional amount of the aqueous composition to the aggregate.

29. The method of claim 15, further comprising providing a growth nutrient.

30. A method for producing construction material comprising:
   providing urease-producing microorganisms, calcium, urea and growth medium in one or more compositions in amounts sufficient to form calcite;
   incubating the one or more compositions with an aggregate plus performance enhancing materials and/or identifiable tags in a formworks; and
   forming the construction material.

31. The method of claim 30, wherein the performance enhancing materials comprise materials for insulation, pollution control, light transmission or combinations thereof.

32. The method of claim 30, wherein the formworks comprises frames, forms, molds, or other apparatus that hold aggregate.

33. The method of claim 30, wherein the construction material comprises porous or non-porous bricks, load-bearing structures, masonry units, veneer, shaped structures and combinations thereof.

* * * * *